United States Patent
Dolfi et al.

[11] Patent Number: 5,174,298
[45] Date of Patent: Dec. 29, 1992

[54] IMAGING PROCESS AND SYSTEM FOR TRANSILLUMINATION WITH PHOTON FREQUENCY MARKING

[75] Inventors: Daniel Dolfi, Orsay; Francois Micheron, Gif-sur-Yvette, both of France

[73] Assignee: General Electric CGR S.A., Issy les Moulineaux, France

[21] Appl. No.: 465,080

[22] PCT Filed: Jul. 1, 1988

[86] PCT No.: PCT/FR88/00356
§ 371 Date: Feb. 27, 1990
§ 102(e) Date: Feb. 27, 1990

[87] PCT Pub. No.: WO89/00278
PCT Pub. Date: Jan. 12, 1989

[30] Foreign Application Priority Data
Jul. 3, 1987 [FR] France ................ 87 09461

[51] Int. Cl.⁵ ............................. A61B 6/00
[52] U.S. Cl. ....................... 128/665; 359/10; 359/30
[58] Field of Search ............. 128/664, 665; 350/3.6, 350/3.67, 3.81, 3.83, 3.85

[56] References Cited

U.S. PATENT DOCUMENTS
3,636,248  1/1972  Korpel .
3,706,965 12/1972  Korpel ................... 350/3.6
3,831,135  8/1974  Smith .
4,284,324  8/1981  Huingard ............... 350/3.85

FOREIGN PATENT DOCUMENTS
2000290  1/1979  United Kingdom .

OTHER PUBLICATIONS
IEEE Transactions on Computers, vol. C-24, No. 4, Apr. 1975, (New York, US), G. Wade et al.: "New Experiments and Analysis in Bragg-Diffraction Imaging", pp. 395–396.

Primary Examiner—Kyle L. Howell
Assistant Examiner—Robert L. Nasser, Jr.
Attorney, Agent, or Firm—Nilles & Nilles

[57] ABSTRACT

In an imaging process and system by transillumination of a medium illuminated by transparency by a beam, an acoustic transducer emits an acoustic wave in the medium which interferes with the beam. The frequency of the light passing through the medium is then shifted from the value of the frequency of the acoustic wave. A collimating device whose object focus is located at the intersection of the acoustic wave and the light beam collects the light diffused by the medium.

24 Claims, 10 Drawing Sheets

FIG.6 composante A(ω) restituée

A: amplitude of optical signal

IMAGING PROCESS AND SYSTEM FOR TRANSILLUMINATION WITH PHOTON FREQUENCY MARKING

The invention relates to a system for imaging an object immersed in a scattering medium or an internal portion (for example a plane) of said scattering object. The system is described in its application to the field of medical imaging. It operates at visible or near-infrared wavelengths and therefore relates to a method of transillumination (or diaphanoscopy).

The essential difference between this system and those known in the technique lies in the fact that the scattered photons taken into account for the formation of the image have an associated frequency which is different from that of the other photons. This difference is obtained directly, within the organ, by Doppler effect. The system therefore permits a tomographic study of the organ.

The method described proposes an alternative to conventional medical imaging systems (x-radiation associated with a film, ultrasonic scanning, nuclear magnetic resonance). It permits the formation of three-dimensional images, which are immediately available, by transmission of visible or near-infrared light through a living organ. This method can also be applied to any scattering medium which is sufficiently transparent to light.

Transillumination as a means of diagnosis was employed for the first time in 1929 for the display of breast tumors. A description of a system of this type will be found in the article "Transillumination as an aid in the diagnosis of breast lesions" by M. Cutler, published in Surgery, Gynecology and Obstetrics, June, 1929. The device employed consisted solely of a lamp placed beneath the patient's breast whilst the medical practitioner directly observed the scattered light. All the devices employed since that time are improvements of this first system. The use of more powerful, cooled torches having sensitive surfaces in the near-infrared region by making use of infrared films or camera, the formation of images having two different wavelengths associated with a substantial treatment of the image, have not permitted a spectacular improvement. The main limitation arises from the very high value of the scattering coefficient within the biological tissues, even at wavelengths in which the absorption is lowest. Devices of this type are employed only for mammography and do not permit detection with any great degree of reliability either of tumors having small lower dimensions (1 cm) or of deep tumors even of larger size.

The method proposed by the INSERM Institute (U238) of Professor Jarry and described in the Doctorate thesis, Science speciality, upheld by S. Debray on June 12, 1987 before the University of Paris, Val de Marne and entitled "Device for laser transillumination of biological tissues, contributions of time resolution and of spectrophotometry" makes it possible to escape from the influence of scattering. The organ is illuminated by a laser beam. The detector placed opposite to the laser, behind the organ, is provided with a collimator. The selection of time of flight or time of traversal of the organ by the non-deviated photons or scattered photons makes it possible to avoid the need to take the scattered photons into account. In fact, in order to select the photons transmitted in a straight line, a pulsed laser is employed. This system also permits spectroscopic analysis of the organ (dye laser). Contrast and perception of details are improved.

The description of such a system will be found in the article "Study in simulation of the behavior of light in biological tissues" by Maarek and Jarry, published in Innovations Techniques Biologiques et Medicales, Volume 7, No. 3, 1985.

The use of a streak camera having a resolution of 5 picoseconds and a pulsed laser source has permitted the development of a tomographic imaging system as described in the article "Laser pulse tomography using a streak camera" by Y. Takguchi et al., published in Proceedings Image Detection and Quality, July, 1986. Tomography is made possible by recording of the backscattered signal. Taking into account the weakness of the signal, this technique will be difficult to transpose to living organs having large dimensions.

The low resolution of conventional systems, even when they are provided with high-performance image processing (Spectrascant process), the complexity of detection systems having higher performances, lead us to propose a transillumination device which does not employ for the formation of images photons transmitted without being scattered but employs instead photons which are scattered in the zone to be imaged. The photons which emerge from this zone are frequency-marked.

In the case of the use of a conventional detector, the very high angular selectivity of heterodyne detection (antenna property) as well as the excellent signal-to-noise ratio achieved make it possible to contemplate its application to the medical field.

If the conventional detection system is replaced by an assembly comprising photorefractive material and solid detector, the image of an internal plane of the scattering organ can be made available instantaneously. In addition, an excellent signal-to-noise ratio is retained.

As described in patent Application GB-A-2000 290, the invention relates to a method of imaging of biological bodies by transillumination in which a medium containing at least one scattering zone is illuminated by transparency by means of a first beam and in which the quantity of light scattered by said scattering zone is measured, wherein there is transmitted in the medium an acoustic wave having a first frequency which interferes with said first beam and wherein there is detected the light which passes through the medium and the frequency of which is shifted by the value of the first frequency.

In accordance with the present invention, in order to solve the problem of signal-to-noise ratio which is inherent in this method, the medium is then subjected to a second acoustic wave having a second frequency which is different from the first frequency.

The invention also relates to a system for imaging by transillumination comprising a laser source which emits a source light beam for illuminating a transparent or translucent medium by means of a first beam as well as a detector for receiving a second light beam resulting from the first beam after passing through said medium, a first acoustic transducer for emitting within the body an acoustic wave having a first predetermined frequency which is not collinear with the first beam as well as an optical collimation device which is placed on the path of the second beam and the object focus of which is located at the intersection of the second beam and of the acoustic wave, frequency filtering means being additionally associated with the imaging system for detecting by means of the detector the light of the second light beam which has been subjected to said translation of the value of the first frequency, characterized in that it comprises a second acoustic transducer (TA2) mounted against the first transducer (TA1), placed on the side opposite to the first light beam (F1) with respect to the first transducer (TA1) and makes it possible to emit a second acoustic wave having a second predetermined frequency (f2) which interferes with the first light beam (F1) but does not interfere with the first acoustic wave and irradiates the entire medium (H) located on the side opposite to the first light beam (F1) with respect to the first acoustic wave.

The different objects and characteristic features of the invention will become more clearly apparent from the following description which is given by way of example with reference to the accompanying figures, in which.

Figure 1:
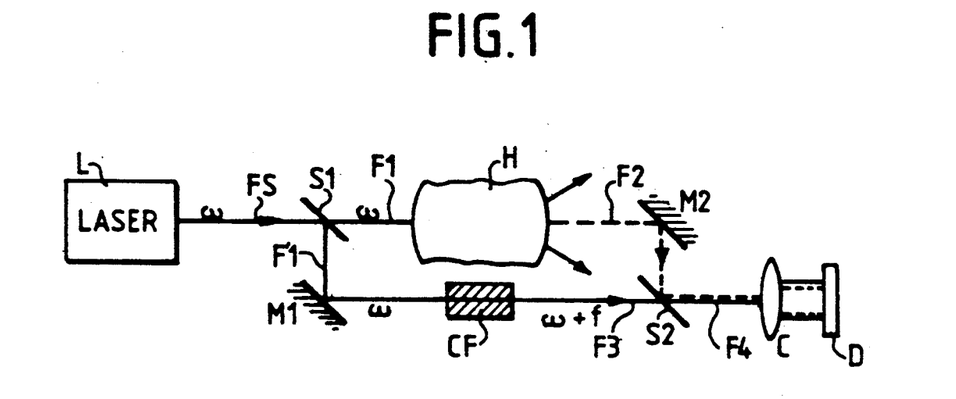
FIG. 1 shows a system for imaging by transillumination to which the invention is applicable.

Referring to FIG. 1, an imaging system to which the invention applies will first be described.

This system comprises a radiation source L which emits a beam FS. By way of example, this beam is a light beam having a frequency $\omega$. A beam-splitter S1 such as a semi-reflecting mirror transmits part of the beam FS to a translucent or transparent body H. This latter receives the beam F1 and retransmits all or part of this beam in the form of a beam F2. This beam F2 is reflected from a mirror M2 to a beam coupler S2. This beam coupler S2 can be a semi-reflecting plate, for example.

The beam-splitter S1 reflects a portion F'1 of the beam FS to a mirror M1. This latter reflects the beam F'1 to a frequency changer CF which delivers in exchange a beam F3 having a frequency $\omega + f$. This beam F3 is transmitted to the beam coupler S2 which combines the beams F2 and F3 and delivers a beam F4 to a detector D. If necessary, an optical element C can focus the light transmitted to the detector D.

In this manner, two light waves F2 and F3 having slightly different frequencies are mixed on a detector.

Figure 2:
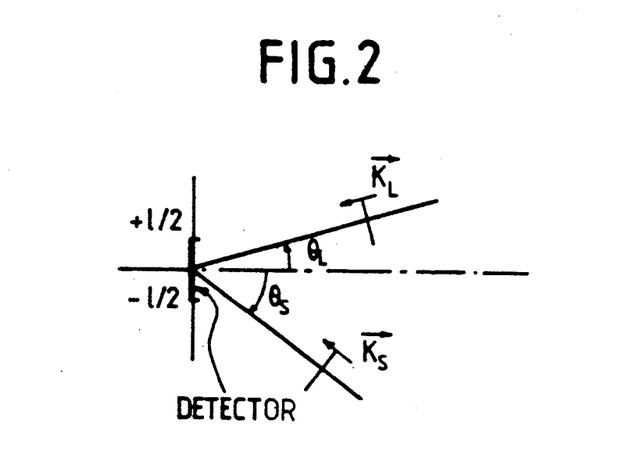
FIG. 2 is an explanatory diagram of the system of FIG. 1.

If, as shown in FIG. 2, there are superposed on a detector two light waves having amplitudes $\overline{U_S}$ and $\overline{U_L}$ having slightly different frequencies $\omega_S$ and $\omega_L$ such that $\omega_S - \omega_L$ is less than a few MHz, there is obtained, in addition to a continuous component, a photocurrent $I_{SL}$ at the intermediate frequency $\omega_S - \omega_L$:

$$I_{SL} = \int 17 \, A \eta (x, y) \, \overline{U_S U_L} dA$$

wherein

A : area of the detector $\eta(x,y)$ : non-uniform quantum efficiency of the detector.

Thus, for a uniform detector, in the case of a plane wave amplifier, we obtain $$I_{SL} \alpha \sin C \left[ \frac{1}{2} (K_L \sin \theta_L - K_S \sin \theta_S) \, l \right]$$

The current at the intermediate frequency therefore has an appreciable value only when $K_L$ and $K_S$ are practically parallel. The first cancellation of $I_{SL}$ takes place in respect of an angular deviation of the order of $\Delta \theta \sim \lambda / l$ with $\lambda$ = wavelength employed $l$ = dimensions characteristic of the zone of superposition ; $i_L$ and $i_S$ being the amplitudes of the photocurrents delivered when the detector receives respectively $U_L$ and $U_S$, we have, in the case of two uniform and parallel plane waves :

$$I_{SL} \alpha \sqrt{i_L i_S} (\cos |\omega_{HL} - \omega_S| t)$$

In a heterodyne detection system, the light waves $U_L$ and $U_S$ will be obtained by splitting a beam delivered by a single source. This is an acoustooptical system (Bragg cell type) which produces the frequency shift $(\omega_S - \omega_L)$ of one wave with respect to the other.

The essential principle of operation of the system of the invention is to obtain this frequency shift, not externally but directly within the organ to be imaged.

Figure 3:
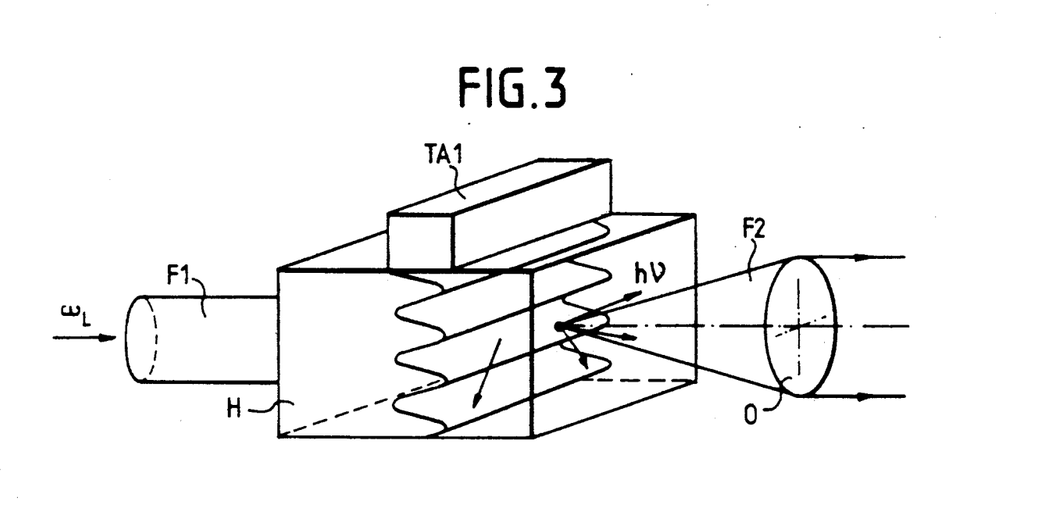
FIG. 3 shows one example of construction of the system for imaging by transillumination with photon frequency marking in accordance with the invention.

FIG. 3 shows how it is possible to generate an acoustic wave within a scattering medium H by means of a transducer TA1 which can, for example, be an acoustic probe similar to those employed in ultrasonic scanning (excitation frequency of 1 to 10 MHz).

A light beam F1 having a frequency $\omega_L$ illuminates the body H.

The photons scattered within the zone delimited by the acoustic probe TA1 interact with the acoustic wave and their associated frequency is therefore, at the first order, shifted from $\omega_L$ to $\omega_S$ if the frequency of the acoustic wave has the value $f = \omega_S - \omega_L$, by reason of the Doppler effect.

The fraction of photons scattered in the zone of propagation of the acoustic wave which passes out of the medium without being subjected to any further scattering, passes into an optical system A. Since it receives the light beam F2, this system can then deliver a plane light wave at the frequency $\omega_S$. This wave is then mixed with a plane wave having the frequency $\omega_L$, in accordance with the tuning conditions described earlier. Mixing is also possible with waves which are not plane but have the same geometrical characteristics.

A very large fraction of photons scattered in the acoustic slice is again scattered before passing out of the scattering medium H. The optical system A, by virtue of the antenna properties of the heterodyne detection, makes it possible to isolate a small volume of scattering organ and to take into account only what is scattered, for example, at the object focal point F of the optical system A. The photons which are scattered subsequently therefore do not take part in the formation of the image. By way of example, the volume of scattering organ F will have a diameter of 100 micrometers to 1 millimeter.

Figure 4:
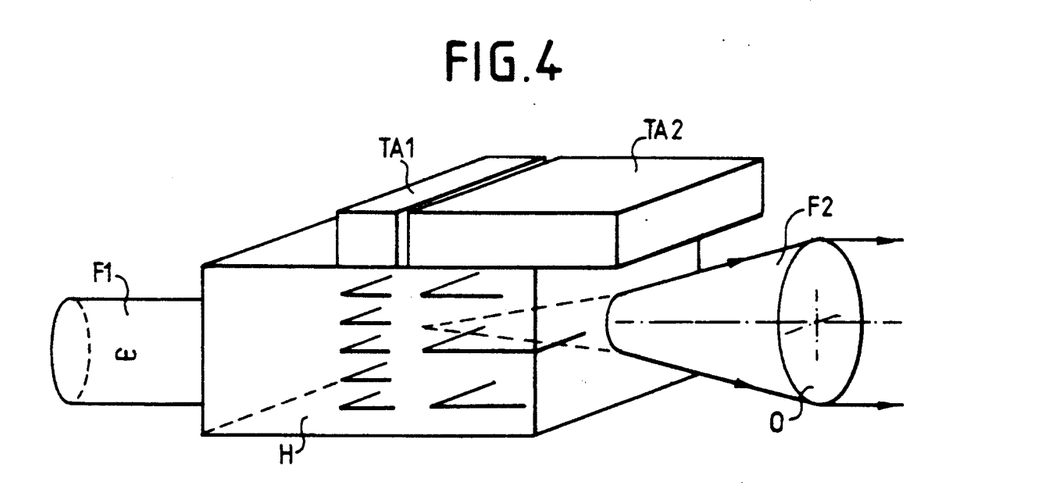
FIG. 4 shows another example of construction of the system for imaging by transillumination in accordance with the invention.

In another embodiment according to the invention as shown in FIG. 4, it is possible to gain freedom from the influence of the photons which are scattered in the "acoustic slice" and again scattered before passing out of the scattering medium. There are employed for this purpose two parallel transducers TA1 and TA2, one of which operates at the frequency f whilst the other operates at the frequency f'. These transducers can be ultrasonic scanning probes, for example.

The photons scattered beneath the transducer TA1 undergo a frequency shift of f and those scattered beneath the transducer TA2 undergo a frequency shift f'. Thus only those scattered beneath the transducer TA1 will have the frequency $\omega+f$ and will produce a photocurrent at the frequency f after mixing with a wave at $\omega$. On condition that they satisfy the antenna theorem conditions, all the others will produce only photocurrents at the frequency $f+nf'$ or $nf'$ according to the number of scatterings sustained. These photons are then readily filtered.

Frequency marking of the scattered photons taken into account for the formation of the image permits isolation of a fictitious plane in a scattering medium H. If the image of this plane is formed point by point, it is apparent that a 3D image will successfully be formed by displacement of the acoustic slice.

Figure 5:
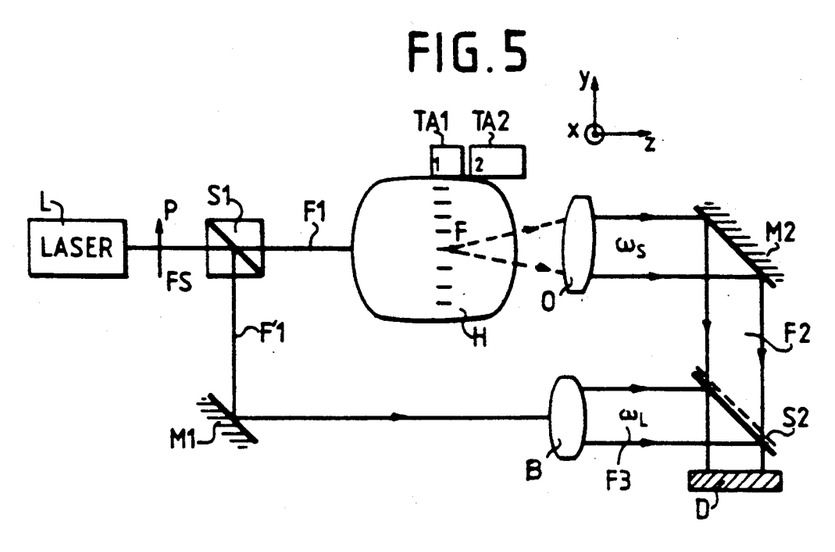
FIG. 5 shows an example of detailed construction of the system of FIG. 4.

FIG. 5 provides a general schematic diagram of this imaging system. In the remainder of the description, the beam at the optical frequency $\omega_L$ will be called the local oscillator and the beam having the optical frequency $\omega_S$ will be called the signal beam. As soon as the local oscillator is sufficiently intense, the heterodyne detection offers, among others, the following advantages:
  detection of high fluxes
  very favorable signal-to-noise ratio by virtue of the very narrow passband which is necessary
  same noise equivalent power as a perfect quantum detector limited by the photon noise.

The same elements as those of FIG. 1 are again found in FIG. 5:
  the source L
  the splitter S1
  the body H
  the mirrors M1 and M2
  the optical coupler S2
  the detector D In addition, there are shown in FIG. 5 two collimating optical systems O and B. The object focal point F of the collimating optical system is located within the body H. There are also shown the acoustic transducers TA1 and TA2 of FIG. 4.

The translations of the optical system O along the axes X and Y permit the point-by-point reconstruction of a plane of PO having a predetermined coordinate along the axis Z and located beneath the transducer TA1. Simultaneous translation of the transducers TA1 and TA2 and of the optical system O along the axis Z from $Z_o$ to $Z_1$ then permits the formation of a two-dimensional (2D) image of the plane of coordinate $Z_1$ along the axis Z. It is to be noted in addition that coincidence of the local oscillator and of the signal is continuously ensured on the detector D.

The system of FIG. 5 therefore makes it possible to form a three-dimensional image of the body H by transillumination by means of a beam F1.

Figure 6:
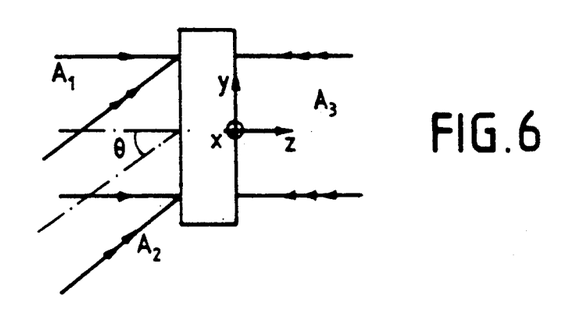
FIGS. 6 and 7 are detailed views of systems for frequency filtering by holography in accordance with the invention.
Figure 7:
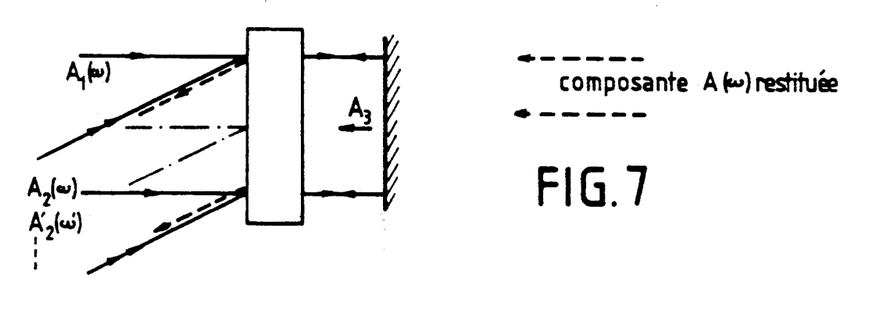

Frequency filtering can be carried out by a system of frequency filtering by holography in real time as shown in FIGS. 6 and 7.

This system as described hereinafter therefore makes use of frequency marking of photons scattered in the zone to be imaged. The principal advantage of this system lies in the real formation of the image of a fictitious plane which is internal to the scattering medium and not simply in the reconstruction of an image by point-by-point scanning of the plane.

If a photorefractive material 1 such as an oxide crystal (BSO, for example) of bismuth and tin, for example, is illuminated with two light waves A1 and A2 as shown in FIG. 6 and such that we have:

$$A_1(x,y) = a_1(x,y) \exp j(\omega t - kz)$$

$$A_2(x,y) = a_2(x,y) \exp j(\omega t - k\theta y - Kz).$$

Its initially uniform transmission is modified and becomes:

$$T(x,y) \alpha |A_1 + A_2|^2$$

$$\alpha 1 + \frac{|A_2|^2}{|A_1|^2} + \frac{A_2^*}{A_1^*} + \frac{A_2}{A_1}$$

The dynamic hologram which has thus been obtained is illuminated simultaneously with a wave $A_3$ such that:

$$A_3 = a_1(x,y) \exp j (\omega t + kz)$$

This wave is identical with the wave $A_1$ and is propagated simply in the opposite direction. When the wave $A_3$ has passed through the hologram, the product $A_3(x,y) \times T(x,y)$ provides the term $$\frac{A_2^*}{A_1} \cdot A_3.$$

This term restitutes a wave which is identical with $A_2$ and which propagates in the opposite direction, that is to say a wave of the form $$\frac{a_2^* a_1}{a_1} \exp j(\omega t + K\theta j + Kz)$$

The wave $A_3(x,y)$ is very readily obtained by interposing on the path of $A_1(x,y)$ after passing through the hologram, a mirror 2 which is parallel to the wave plane of $A_1(x,y,\omega)$ as illustrated in FIG. 7.

When the photosensitive plate is illuminated with a plane but polychromatic wave $A_2$, $A_2 = A_{2(\omega)} + A'_{2(\omega')} + \ldots$, and a monochromatic wave $A_{1(\omega)}$, only the component $A_{2(\omega)}$ will contribute to the formation of a system of stable fringes. After interference with $A_1$, the components of $A_2$ whose frequency differs from $\omega$ will produce only systems of fringes having a rate of travel which is too high to be taken into account by the material. Restitution by $A_3(\omega)$ makes it possible to isolate the component $A_2(\omega)$. The hologram can therefore be considered as a frequency filter.

This method of filtering can be employed for isolating, in the light scattered by the organ, the component at the frequency $\omega_S$, that is to say the photons scattered beneath an acoustic transducer which is similar to that described earlier.

Figure 8:
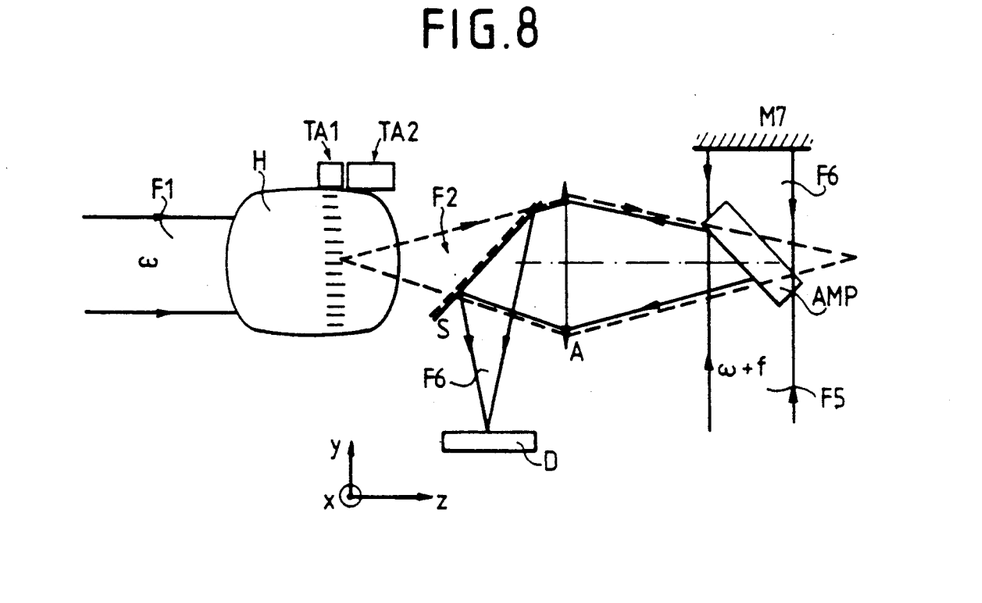
FIG. 8 shows an example of construction of the system of the invention comprising an optical amplifier.

FIG. 8 gives an example of construction of a system of this type. Only the component of light scattered at $\omega + f$ interferes with the pumping beam on the AMP material which serves to produce a dynamic hologram. The beam which emerges from the mirror M7 then restitutes this component of the beam scattered at $\omega + f$. A semi-transparent plate S makes it possible to form, for example on a photographic film D, the image of the fictitious organ slice located beneath the transducer TA1 which vibrates at the frequency f. As has been seen earlier, the transducer TA2 which operates at the frequency f' makes it possible to escape from the influence of the photons scattered in the zone to be imaged and subsequently re-scattered. By simple translation in a direction parallel to the axis Z of the assembly constituted by:

the optical device A
the semi-transparent plate S
the amplifying material AMP
the detector D, it is possible to image different successive slices of the organ and subsequently to reconstitute a three-dimensional image of this latter.

The systems of the present description have a source which is capable of emitting successively at several wavelengths. This permits spectroscopic determination of the image formation medium at different wavelengths. The two systems form images which take into account both absorption and scattering coefficients of the medium at the same time.

The source must be sufficiently coherent in time to permit mixing on the detector D. A laser source is suitable. This source can be monochromatic, can supply discrete wavelengths or a continuous spectrum (dye laser at each wavelength permits the formation of an image).

It will be possible to associate with each type of detector D one or a number of types of illumination and scanning of the organ or medium H whose image is to be formed. When two beams of different sizes interfere on the detector, only that part of this latter which is limited by the narrowest beam generates a signal at the intermediate frequency f. The angular selectivity is limited by the size of the narrowest beam.

The imaging system described permits measurement of the light flux scattered by a small volume of organ whose position is known, hence the possibility of reconstruction of the image.

Figure 9:
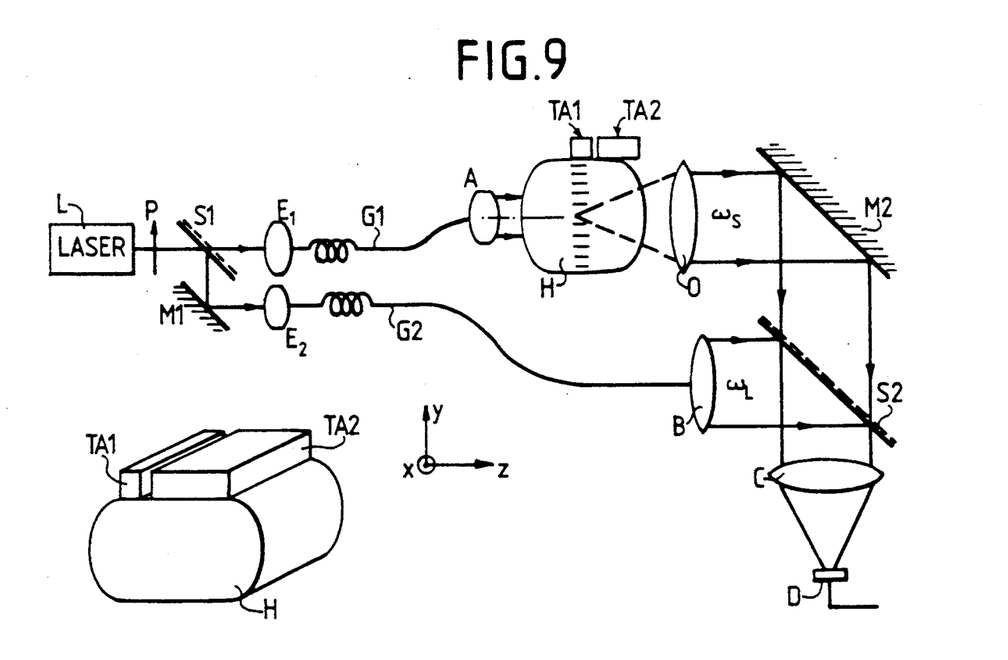
FIG. 9 shows an example of construction of the system of the invention comprising optical transmission waveguides ; imaging system with optical guides as applicable to the system of FIG. 9.

In FIG. 9, the light emitted by the source L is linearly polarized by a polarizer P, then split into two channels by a splitter S1 which can be a semi-reflecting plate or a splitter cube. It can be a dissymmetrical system having, for example, a transmission T=0.9 and a reflection R=0.1. There is thus provided a beam which is more powerful for illumination and an oscillator which does not dazzle the detector.

The optical systems $E_1$ and $E_2$ adapt the geometry of the laser beam to that of optical transmission fibers $G_1$ and $G_2$.

These fibers $G_1$ and $G_2$ serve to connect the source L to the system for illuminating the medium H and to the optical coupler S2.

The optical systems A and B are optical systems which are adapted to the exit of the fibers $G_1$, $G_2$ and deliver collimated beams. The beam which emerges from A has small dimensions (diameter of 1 to 10 mm) so as to permit a fairly high illumination power density.

The optical system 0 permits collection of the photons scattered beneath the transducer TA1 at the frequency f and collimation of the wave thus obtained. The axes of the optical devices 0 and A coincide.

Mixing of the local oscillator wave at the frequency $\omega_L$ and of the signal wave at the frequency $\omega_S$ is carried out on a semi-transparent system S2.

The optical system C makes it possible after mixing of the two waves to adapt their size to that of the detector D. The noise-generating surface is reduced to a maximum since it coincides with the signal-generating surface.

The detector is of the photodiode type but can be replaced by a photocathode or a photomultiplier, depending on the applications.

$M_1$ and $M_2$ are mirrors or total-reflection prisms.

The acoustic transducers TA1 and TA2 are transducers, for example of the ultrasonic scanning probe type, which deliver a practically collimated acoustic wave. The transducer TA1 makes it possible to excite an organ slice, the thickness of which is of the order of 1 mm to 10 mm. The transducer TA2 which makes it possible to gain freedom from the influence of the multiply scattered photons, must excite acoustically the entire organ located beyond TA1.

The image of an acoustically cut slice is then obtained by simple translations of the imaging system (A, O, $M_2$, B, S2, C, D) along the axes X and Y. Coincidence between signal and local oscillator is continuously ensured while these translations take place.

The selection of the different successive planes, the image of which is to be formed, is achieved by translation along the axis Z of the assembly constituted by the transducer TA1, the transducer TA2 and the optical system O.

The light fluxes obtained from each slice are very different according to the abscissa along the axis Z. They increase when this abscissa increases, hence a necessary variation of the gain of the amplifier which follows the detector.

Figure 10:
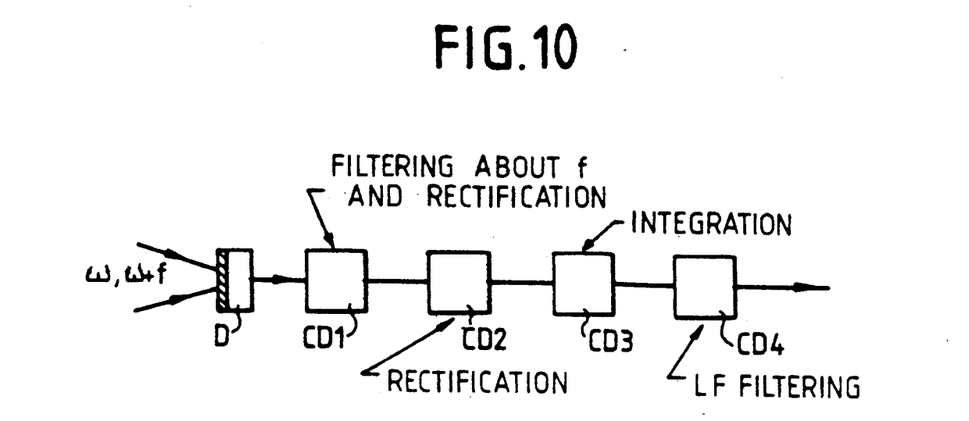

The detection chain is shown in FIG. 10.

This chain comprises the following different circuits connected in series to the detector D:

a filtering and amplifying circuit CD1;
a rectifying circuit CD2;
an integrating circuit CD3;
a low-frequency filter CD4.

The frequency $\omega_L$ is that of the laser source and therefore of the local oscillator beam; $\omega_S = \omega_L + f$ is the frequency of the signal beam.

In FIGS. 11 to 19, there is shown the waveform of the signals at different points of the system.

Figure 11:
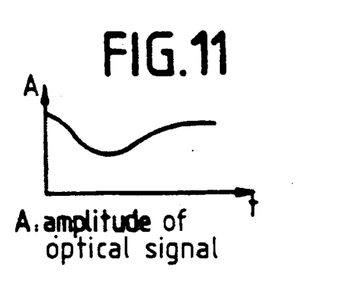
Figure 12:
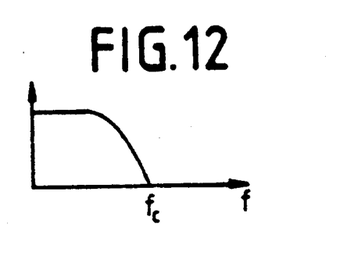

FIGS. 11 and 12 show respectively the progressive variation of the amplitude of the optical signal during a scanning line and the low-frequency spectrum of this progressive variation.

The frequency $f_C$ can be assimilated with a spatial frequency. It puts a figure to the transverse resolution of the system at the time of scanning of the scattering object.

Figure 13:
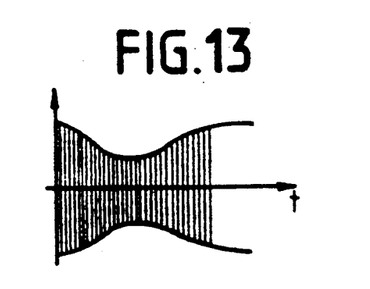

FIG. 13 represents the electromagnetic wave which constitutes the carrier of the signal obtained during one scanning line (the electromagnetic wave at the frequency ω).

Figure 14:
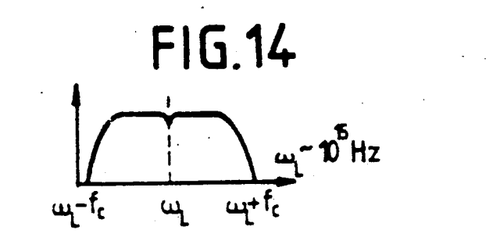

FIG. 14 gives the spectrum of this wave. This is the signal wave.

Figure 15:
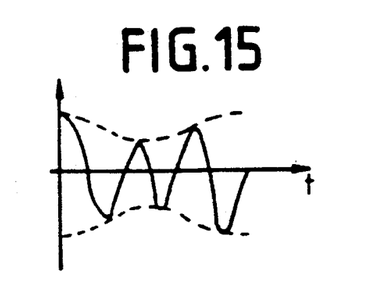
Figure 16:
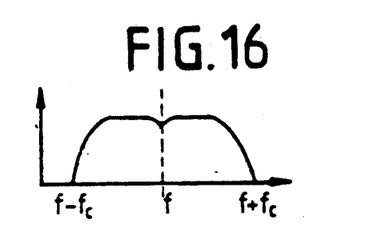

FIGS. 15 to 16 represent the signal having an intermediate frequency f detected by the detector D and the associated frequency spectrum. This signal is obtained after mixing of the signal beam and of the local oscillator (output of CD1).

Figure 17:
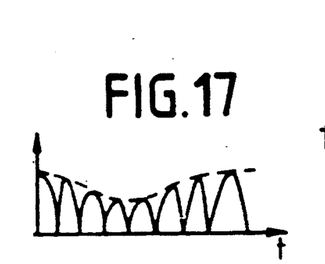
Figure 18:
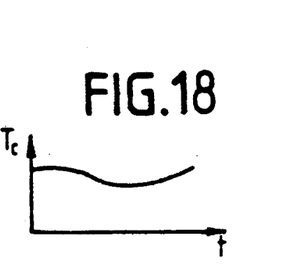

FIGS. 17 to 18 represent the signal which is rectified then filtered by the circuits of the detection chain (respectively at the output of CD2 and of CD3).

Figure 19:
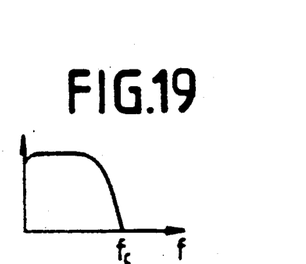

FIG. 19 represents the frequency spectrum at the output of CD3.

Figure 20:
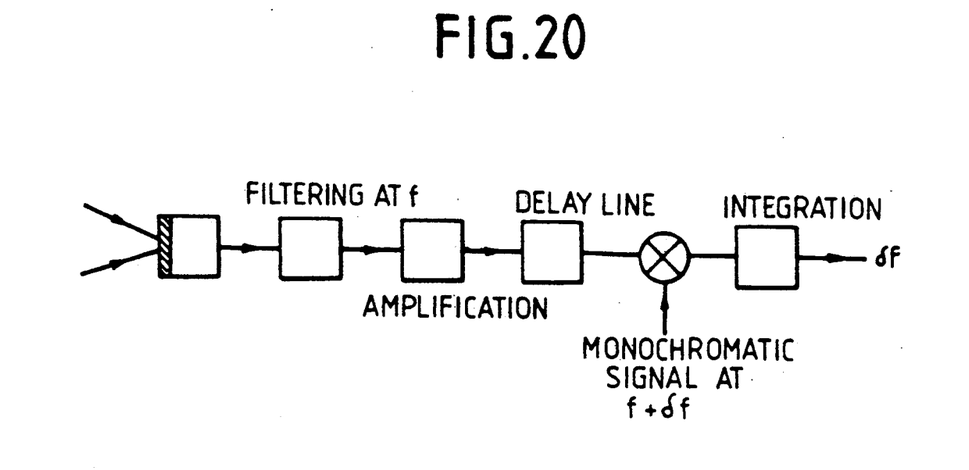

FIG. 20 provides an alternative form of construction of the circuits of FIG. 10.

This variant achieves an improvement to the detection chain by reduction of the passband.

To this end, a delay line CD5 followed by a logic gate CD6 controlled by a signal having a frequency $f+\delta f$ are interposed between the rectifying circuit CD2 and the integrating circuit CD3. The intercorrelation permits integration which supplies a signal having a frequency $\delta f$ which is distinctly lower than the frequency f.

In an alternative embodiment of the system of FIG. 9, if the collimated beams emerging from O and B have a diameter which is comparable with that of the detector D, it is possible to dispense with the optical system C. The detector is then exposed to two superposed plane waves.

Figure 21:
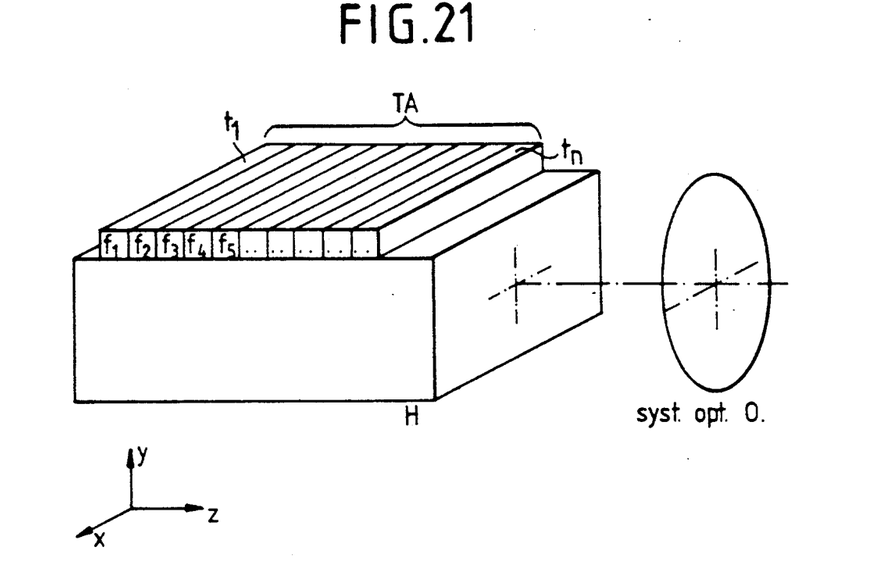

Reference being made to FIG. 21, an alternative form of construction of the transducers will now be described.

It is possible in fact to frequency-mark all the photons scattered within the organ H and also to suppress the translations of the transducers which are necessary for the formation of the image. FIG. 21 illustrates a system of this type. The transducer TA comprises a number of acoustic probes T1 to Tn. Each acoustic probe is excited at a frequency which is different from its neighbors. A photon scattered beneath the transducer $T_i$, vibrating at $f_1$, is associated with a light wave having a frequency $\omega + f_i$ and therefore produces a photocurrent at the frequency $f_i$. With each abscissa along the axis Z, it is thus possible to associate a frequency $f_i$. When the focusing of the optical system O passes from $Z_i$ to $Z_{i+1}$, it is only necessary to change the center frequency of the filter CD1 which is connected to the detector D, from $f_i$ to $f_{i+1}$.

The photons which can be scattered beneath a transducer TAi so as to produce a photocurrent at the frequency $f_i$ are those which have reached the abscissa $Z_i$ without being scattered. They are always associated with the optical frequency ω. The photons which take part in the formation of the image of the plane of abscissa $Z_1$ are those which are scattered at this abscissa and pass out of the scattering medium without being again scattered.

Optical frequencies of the type $\omega + f_i + f_{i+1} + \ldots$ are associated with the multiply scattered photons. In order to differentiate the abscissae $Z_i$ perfectly, it is therefore only necessary to provide filters at the frequencies $f_i$, through which the frequencies resulting from the sum of several frequencies $f_i$ are not allowed to pass.

The form of construction of the transducers shown in FIG. 21 can be adapted to the different alternative embodiments of the invention which will now be described.

In an alternative embodiment which is not shown in FIG. 9, said collimated beam produced by the optical system A has a sufficiently large diameter to cover the entire zone whose image is to be formed. The system for illuminating fibers and optical system A of the zone as well as the optical system 0 no longer need to be translated. A possible non-uniformity of illumination of the zone can be taken into account by a first low-quality "reading" of the acoustic slice to be imaged.

In another alternative embodiment of the invention, the optical paths are no longer carried out in fibers. These latter are replaced by systems of translation TR1 and TR2 of the beams shown in FIG. 22.

Figure 22:
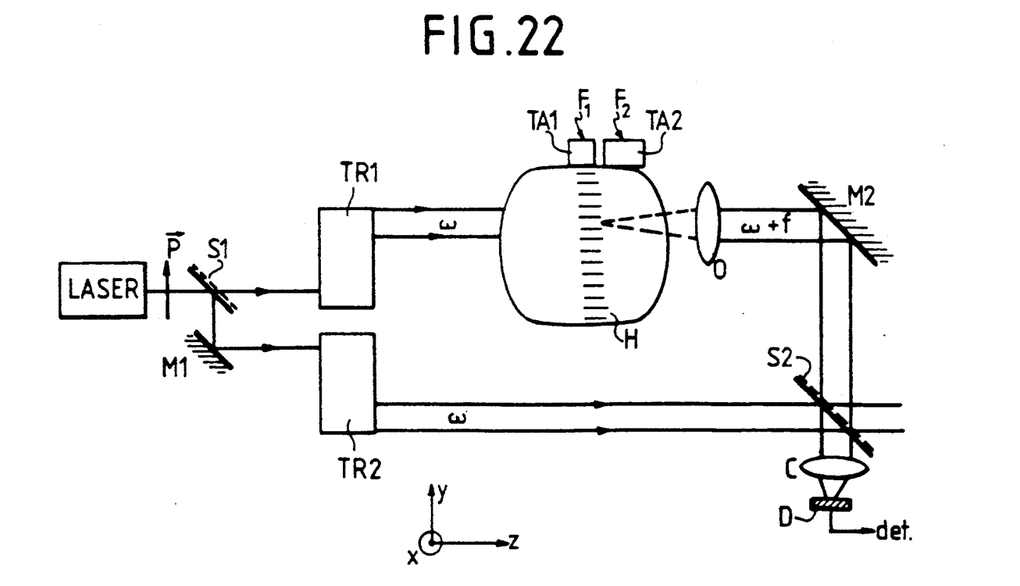
Figure 23:
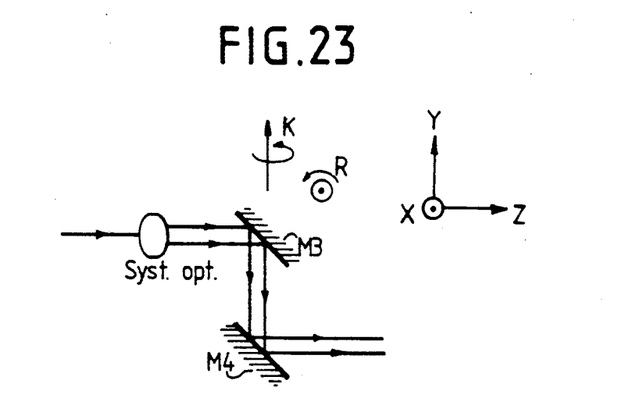

The systems TR1 and TR2 carry out the translations along the axes X and Y and the shaping of the illumination, beam F1 and local oscillator beam F'1. These systems TR1 and TR2 are, for example, systems comprising two mirrors M3 and M4 which rotate in continuously parallel relation as shown in FIG. 23. The general movement of the two mirrors is either a rotation about an axis R, which produces a movement of translation along the axis X, or a rotation about an axis K, which produces a movement of translation along the axis Y.

The displacements of the systems TR1 and TR2 are synchronized with those of the assembly (O, M2, S2, C, D) so as to maintain coincidence of the signal and of the local oscillator.

The systems TR1 and TR2 can be constructed differently with prisms, for example.

Figure 24:
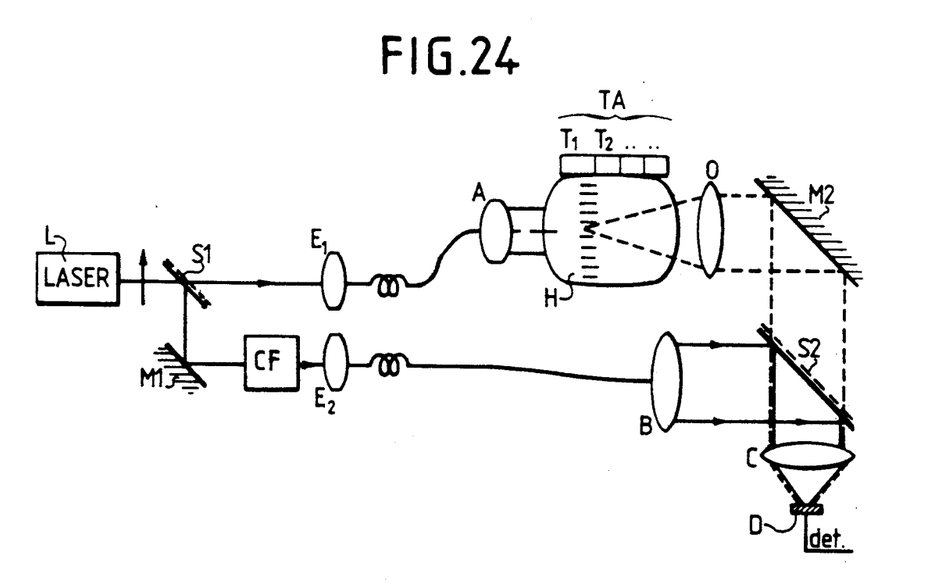

FIG. 24 illustrates an imaging system comprising heterodyne detection means which include a beam splitter S1 for dividing the beam delivered by the source L into two beams F1 and F'1. The beam F'1 is reflected from a mirror M1 to a frequency changer CF which produces in exchange a beam F3 having a frequency $\omega + f$. The beam F3 is transmitted to the coupler S2 which combines the beams F2 and F3 to the detector D. As described with reference to FIG. 1, there is thus carried out a mixing of two light waves F2 and F3 having different frequencies on the detector D.

In order to ensure that the photons scattered within the acoustic slice created by the transducer T1 and subsequently re-scattered are not taken into account, the antenna properties of the heterodyne detection are thus employed. Any light scattered at any point other than the object focus of the optical system O is not collimated in the direction of the local oscillator and does not contribute to the component of the photocurrent at the frequency f.

The system of FIG. 24 thus operates with a single transducer T1.

However, the use of a plurality of transducers (T1, T2, . . .) or of one transducer having multiple frequencies TA as shown in FIG. 24 can be accompanied by the use of a system CF which is capable of shifting the frequency of the local oscillator.

When the optical system O scans the acoustic slice located beneath a transducer $t_i$, a light wave having the frequency $\omega + f_i + \delta f$ is generated at the output. Thus the observed photocurrent no longer has a different frequency according to the abscissa which is taken into account but always has the frequency $\delta f = (\omega + f_i + \delta f) - (\omega + f_i)$.

The detection chain of FIG. 10 thus has a narrow passband ; the filter and the amplifier CD1 are optimized by a single frequency. The frequency shift system CF can be of different types, for example :

acoustooptical modulator controlled by a direct-current voltage (Bragg cell);

mirror M1 mounted on piezoelectric material which is excited by a sawtooth voltage;

half-wave plate in rotation between two quarter-wave plates.

The first solution entails the need for a position control of the acoustooptical system. In fact, when the excitation acoustic frequency changes, it is necessary to modify the beam input incidence on the system CF in order to retain good diffraction efficiency.

The second solution is less complex but does not readily supply the frequencies necessary for good tuning between signal and local oscillator. Only those acoustic waves which have a frequency of 2 to 7 MHz pass through the biological media without excessive absorption.

The third solution permits only monochromatic operation.

In the medical application of the system, the first solution is mandatory.

In the case of other scattering media which do not call for frequencies of the order of 1 MHz, the two other solutions are suitable.

These remarks remain valid in the case of the device MA employed in the system described hereinafter.

In the different forms of construction described earlier, the beams which emerge from the optical devices 0 and B may not be collimated. The signal and local oscillator waves are not in that case necessarily plane but must have the same geometrical characteristics.

Similarly, it can be considered that the optical systems are of circular shape in the conventional manner but they can also be of cylindrical shape. Thus the optical systems 0, B and C are accordingly cylindrical, the generator-lines of the cylinders being parallel to the direction of the transducer TA1. The translation of the system along the axis X is thus suppressed. The system C forms a light line and scanning of this latter by a detector which moves in a direction parallel to the generator-lines permits the formation of one line of the image of the fictitious plane $P_o$ cut by TA1. The detector in translation can be replaced by a line of detectors (photodiode strip parallel to the generator-lines, each detector being read in turn).

The system of the invention also provides for the use of a conjugate mirror.

Figure 25:
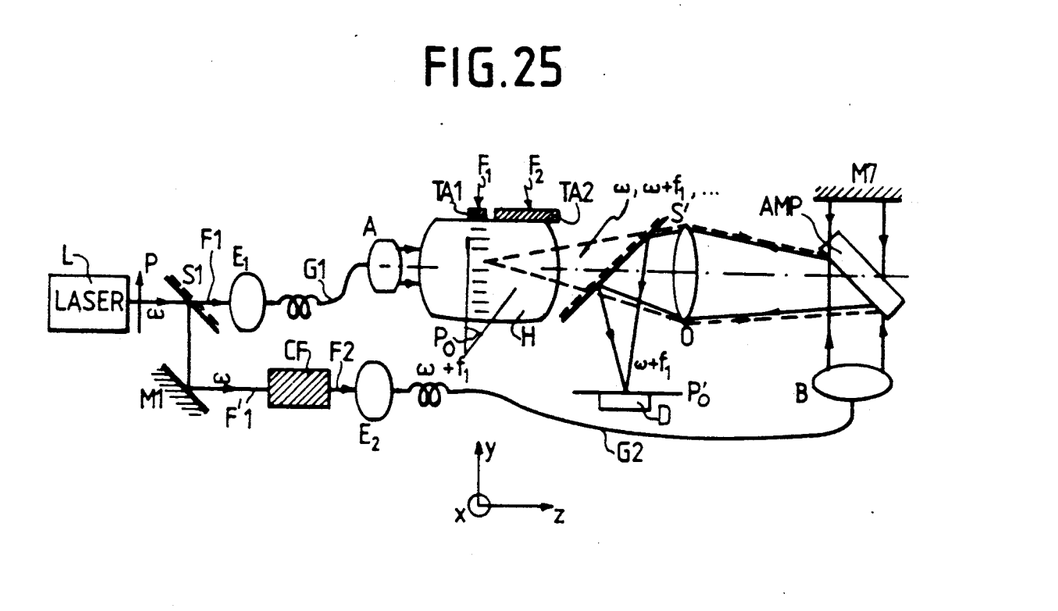
FIG. 25 shows an imaging system with amplification in accordance with the invention.

The system illustrated in FIG. 25 permits the formation on a plane $P'_o$, of the image of a defined plane $P_o$, by the transducer TA1.

There are again shown in FIG. 25 the same elements which bear the same references as in the systems described earlier.

The transducer TA1, excited by a signal having a frequency fl, produces an acoustic wave having a frequency fl. The frequency changer CF, starting from an optical signal having a frequency $\omega$ delivers a signal having a frequency $\omega + fl$ to the device AMP.

The plane $P'_o$ performs the function of detector D and the received image P' is memorized either:

directly on a film contained in the plane $P'_o$ and developed subsequently;

or by scanning of the plane P' by a point detector in translation along the axes X and Z;

or by scanning along the axis X, of a linear multiple detector (strip of photodiodes, for example) or of a matrix detector arranged along the axes X and Z and in translation along these axes;

or directly by a detection system having large dimensions, of the CCD or Vidicon type, for example (video camera).

The device P is a linear polarizer which determines the possible polarization of the laser source.

S is a non-polarizing beam-splitter system. Depending on the power density which is necessary for illumination, the transmission of S can be chosen between 50 and 90% (complementary reflection at 100%).

The devices $E_1$ and $E_2$ are optical systems which adapt the geometrical characteristics of the laser beam to those of the optical fibers G1 and G2 employed.

The frequency-changer system CF is a system which translates the frequency of the beam F'1 from $\omega$ to $\omega + fl$. By way of example, this can be an acousto-optical modulator controlled by a direct current. The mirror M1 can be position-controlled so as to ensure that the beam at the exit of CF is of maximum intensity. This frequency shift can also be obtained directly on M1 if this latter is cemented to piezoelectric material excited by a sawtooth voltage or by a system of quarter-wave and half-wave plates in rotation.

The optical devices A and B are optical systems which are adapted to the output of fibers and which produce collimated beams. The dimensions of the illuminating beam which emerges from A are comparable with those of the image which it is desired to form.

In the case of scattering objects having large dimensions, it is not always possible to form the image of the entire plane P. This image is in that case reconstituted by juxtaposition of successive photographs obtained by simultaneous displacements along the axes x and y of A and of the assembly (S', O, AMP, M7, B).

The different planes P which are internal to the scattering medium are imaged by simultaneous translations of TA1, TA2 and of 0 along the axis Z. A displacement of P' along the axis y is then necessary in order to restore correct focusing.

The wave emerging from 0 is weakly focused on the optical amplification device AMP so as not to form therein a lattice having a pitch which is too small (smaller than the spatial frequency permitted by the material).

As in the system described earlier, the transducers TA1 and TA2 are transducers (frequency of 1 to 10 MHz) which may be of the ultrasonic scanning probe type, for example.

The optical amplifier AMP is cut in photorefractive material of the type employed in dynamic holography (BSO, BGO, $BaTiO_3$, GaAs ...).

Continuous photocurrents are measured at the output of the detectors which carry out point-by-point scanning of the image. The light fluxes obtained from each slice are very different according to the abscissa along the axis Z. They increase when the abscissa along the axis Z increases, whence the need for adaptation of the sensitivity and gain of the amplifier according to the detector.

It is possible under certain very specific conditions to make use of a conjugate mirror having a coefficient of reflection higher than 1.

As described in the article "Amplified phase conjugate beam reflection by four wave mixing with photorefractive Bi SiO crystals" by H. Rajbenbach and J. P. Huignard, published in the Journal of Optical Society of America of Aug. 28, 1984.

The frequency translation system CF then no longer delivers a wave at the frequency $\omega + f_1$ but at $\omega + f_1 + \delta f$, with the result that there is a gain on reflection in all the following variants.

In the example of construction of FIG. 25, the transducers TA1 and TA2 can be replaced by a series of transducers $T_1 \ldots T_n$ which vibrate at the frequencies $f_1, \ldots f_N$. The frequency translation system CF of FIG. 25 must also produce these frequencies. As has been seen from the description of FIG. 21, a device of this type makes it possible to determine the abscissa of scattering of singly-scattered photons. Focusing of 0 on the abscissa $Z_i$ along the axis Z (abscissa marked by the transducer $T_i$) as well as a frequency translation of $f_i$ as produced by CF make it possible to obtain the image of the plane $P_i$. If the beam which emerges from O and illuminates the device AMP of FIG. 25 is collimated or very slightly focused, it is not necessary to ensure that (M2, AMP, B) accompanies the optical system O during its translation along the axis Z.

Figure 26:
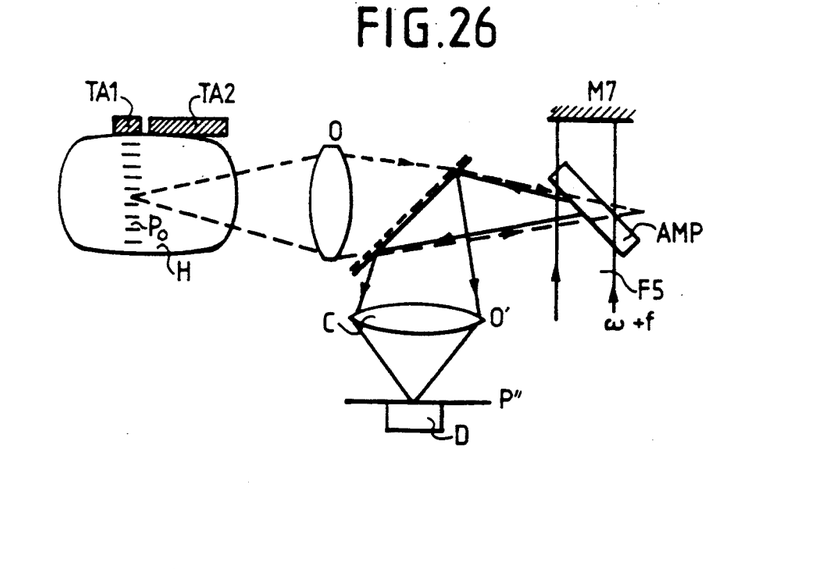
FIG. 26 is a detailed view of the system of FIG. 25.

In an alternative embodiment of this system as shown in FIG. 26, the optical systems O and S' are reversed. It is then necessary to add to the system an optical element O' which permits the formation of the image on a plane P''. This optical element O' makes it possible during scanning of 0 along Z to continuously form the image of P at P'' having a fixed abscissa Y. The detection system therefore no longer needs to move along the axis Y.

In the system of FIG. 25, it can also be envisaged that the optical paths are no longer carried out within fibers. These latter are accordingly replaced by beam translation systems as described with reference to FIGS. 22 and 23.

In different forms of construction described earlier, the displacements of the acoustic probes TA1, for example, and of the optical systems, are simultaneous. However, they may be decorrelated. In this case the medical practitioner who is handling the acoustic probes can thus partly determine the position of the cut by optical viewing. This handling operation makes it possible a priori to choose the examination zone, this latter being then scanned automatically.

It is possible to employ ultrasonic transmitters other than the single probes proposed in the foregoing. Sector scanning probes make it possible, for example, to combine the optical and acoustic scans of the zone to be imaged.

Figure 27:
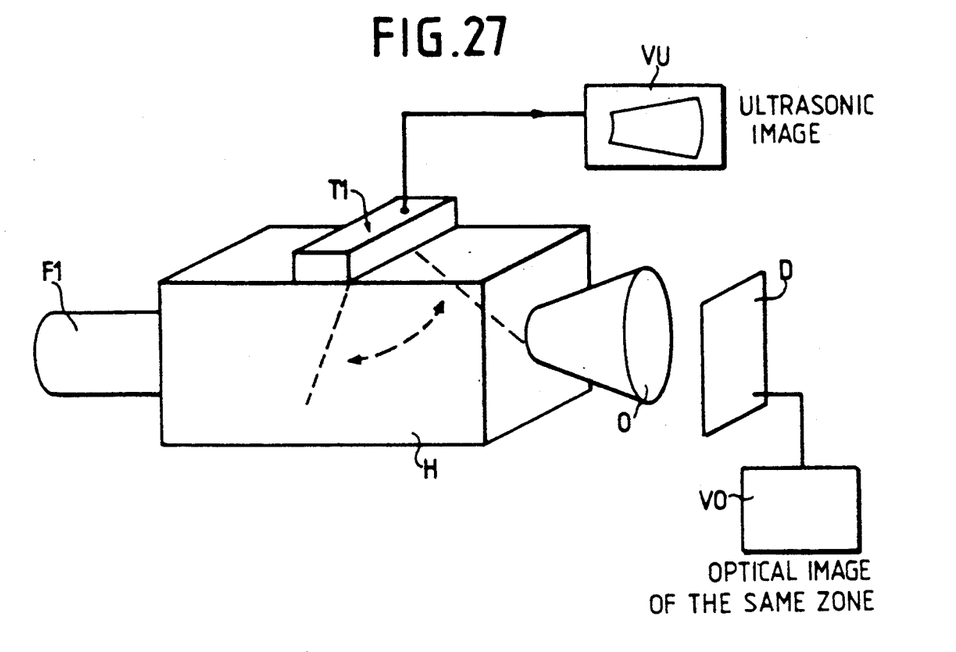
FIG. 27 shows a combined optical and acoustic imaging system in accordance with the invention.

The use of ultrasonic scanning probes as transducers makes it possible to obtain two images, one image being optical (transillumination), the other being acoustic (ultrasonic scanning). The second image makes it possible, for example, to choose the zone whose optical image is to be obtained, as shown in FIG. 27. There can be seen in this figure the ultrasonic image obtained by the probe T1 in the medium H and displayed on a visual display device VU connected to the probe T1. The detector D makes it possible to obtain an optical image of the same zone and displayed on another visual display device VO connected to the detector D.

A double-imaging process of this type is of undoubted clinical interest. In fact, the same homogeneities do not offer the same contrast in the two images, depending on the wavelength of investigation, whether acoustic or optical.

The ultrasonic scan has only low resolution but supplies images which can be readily interpreted in the present state of the art. The expected resolution of the transillumination is much better but the first images obtained will be significant only if they can be compared with the interpretable images produced in the same zone by a different method. The complementarity of the two modes of imaging therefore appears at several levels.

By analogy with ultrasonic scanning, it can be an advantage to detect the backscattered optical signal. It is also possible to form two complementary images, one by transmission and the other by backscattering.

It has in fact been observed that, in a biological medium, a scattering element scatters the light which it receives in all directions. In particular, a scattering element contained at the point F of the medium H of FIG. 28 scatters in the direction Z as has been seen earlier but also scatters the light in the direction Z'.

Figure 28:
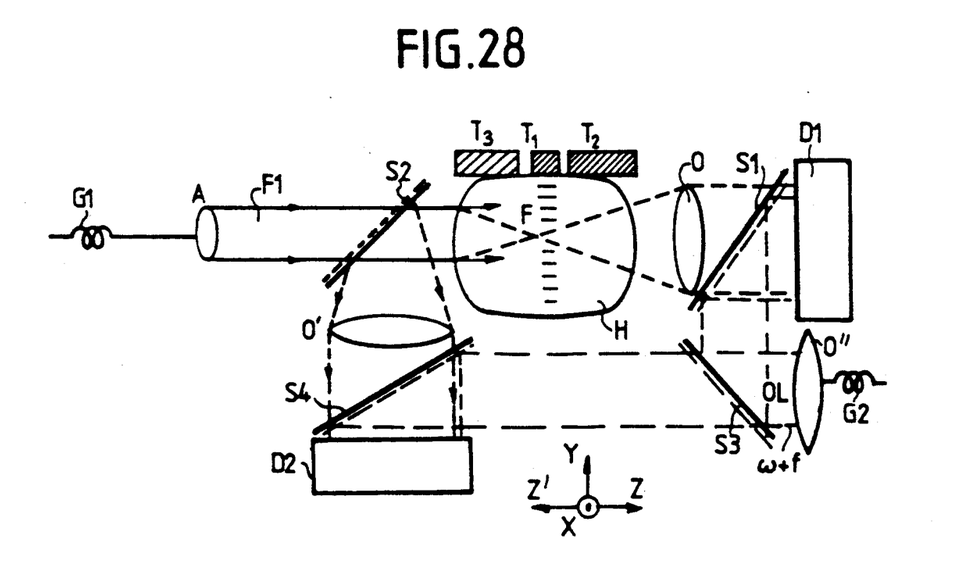
FIG. 28 shows an imaging system with backscattered images in accordance with the invention.

In another example of construction in accordance with the invention as shown in FIG. 28, it is proposed to interpose a semi-reflecting plate S2 between the source L and the body H on the path of the beam F1 which illuminates the body H.

A lens O, the object focus of which is located at the point F receives the light scattered by the point F and transmits this light to a first detector D1. This arrangement has been described earlier.

A lens O' receives the light which is back-scattered by the point F and reflected from the semi-reflecting plate S2. The image of the object focus of the lens O' through the semi-reflecting mirror S2 is also placed at the point F. The backscattered light is transmitted by the lens O' to a second detector D2. The backscattered signal is therefore scanned in a manner which is wholly similar to the scattered wave. The two detectors D1 and D2 therefore both detect the scattering point F. By adding (by means not shown) the results of detection of the two detectors D1 and D2, higher sensitivity of detection is thus obtained.

The system of FIG. 28 can operate with a single transducer T1 in a manner which is similar to the system of FIG. 3. It can also operate with the transducers T2 and T3 located on each side of the transducer T1.

The transducers $T_2$ and $T_3$ which deliver a frequency which is different from that of $T_1$ make it possible to take into account only the photons which are scattered at F and pass out of the medium without further scattering.

The system of FIG. 28 can give rise to different alternative forms of construction by combining therewith different arrangements described earlier. The intensity of the fluxes scattered and backscattered from F is measured by heterodyne detection. These fluxes are superposed on a local oscillator before being detected on D1 and D2 (see FIG. 28).

It is wholly apparent that the foregoing description has been given solely by way of non-limitative example. Other variants can be contemplated without departing from the scope of the invention. In particular, different arrangements described earlier can be combined with each other.

We claim:

1. A transillumination imaging method comprising:
   transmitting a first light beam (F1) into at least one scattering zone within a medium (H) to be imaged;
   transmitting into said scattering zone within said medium at least first and second acoustic waves having a first frequency ($f_1$) and a second frequency ($f_2$), respectively, wherein the first frequency ($f_1$) and the second frequency ($f_2$) are different and the at least first and second acoustic waves interfere with the first light beam (F1), with the second acoustic wave interfering with the first light beam after the first acoustic wave interferes with the first light beam, thereby producing a second light beam (F2) produced by interference of said first and second acoustic waves with said first light beam;

producing a reference beam to interfere with the second light beam; and applying said second light beam and said reference to a detector and measuring a quantity of light scattered by said scattering zone by detecting a light which has been subjected to a translation of the first frequency ($f_1$) and the second frequency ($f_2$).

2. Method according to claim 1, further comprising:

transmitting into the scattering zone of said medium a number of first acoustic waves having different frequencies ($f_1, f_2, \ldots f_i$) which each interfere independently with the first light beam (F1); and successively detecting light which has been subjected to translations of each of said frequencies ($f_1, f_2, \ldots f_i$).

3. Method according to claim 1, wherein said step of producing a reference beam comprises:

producing a light beam having a frequency which is slightly shifted with respect to the frequency of the first light beam.

4. A system for transillumination imaging of a medium comprising:

laser means for illuminating a scattering zone in the medium by means of a first laser beam having a first frequency (F1);

at least first and second acoustic transducers mounted adjacent to each other for emitting within the medium respective acoustic waves which are not collinear with the first laser beam and which have respective predetermined frequencies ($f_1, f_2$), said acoustic waves intercepting and interfering with said first laser beam (F1) in said scattering zone;

an optical collimator, placed in the path of said first laser beam and having an object focus located at said scattering zone in said medium for collimating light of said first laser beam which is intercepted by said acoustic waves from said at least first and second acoustic transducers, which produces a collimated second laser beam (F2);

said laser means comprising means for producing a reference laser beam (F3) to interfere with said second laser beam; and a detector optically coupled to said reference laser beam and said collimated second laser beam for measuring the quantity of light scattered in said scattering zone, including frequency filtering means for detecting light of the collimated second laser beam which has been subjected to a frequency translation relative to said first frequency due to interference with said first and second acoustic waves;

said second acoustic transducer mounted adjacent the first acoustic transducer and positioned on the opposite side of the first transducer with respect to the side of the medium on which the light beam is incident, the second acoustic wave emitted by said second transducer interfering with the first light beam but not interfering with the first acoustic wave and irradiating the medium downstream of where the medium is irradiated by said first acoustic wave with respect to the side of the medium on which the first light beam is incident.

5. The system according to claim 4, comprising:

a plurality of said acoustic transducers for producing a plurality of acoustic waves having respective frequencies ($f_1, f_2, \ldots f_i$) and which are located successively displaced along a path of said first laser beam and which transmit respective acoustic waves into said respective portions of said medium in the path of said first laser beam.

6. Imaging system in accordance with claim 4, wherein said laser means comprises:;

a source laser for producing a source beam (FS):

beam splitter means, which is placed on the path of said source beam (FS), for dividing the source beam so as to provide said first laser beam (F1) and said reference laser beam (F3), and beam coupler means for retransmitting to the detector (D) said reference laser beam (F3) and the second beam (F2) which emerges from the medium (H).

7. Imaging system in accordance with claim 6, wherein said laser means comprises a frequency shifting device (CF) which is placed between said beam splitter means and said detector for producing said reference beam with a frequency which is slightly displaced with respect to the frequency of the first beam (F1).

8. Imaging system in accordance with claim 7, wherein the frequency shifting device (CF) comprises an acoustooptical system.

9. Imaging system in accordance with claim 7, wherein the frequency shifting device (CF) comprises a mirror (M2) mounted on a piezoelectric device.

10. Imaging system in accordance with claim 4, comprising:

a holographic filtered device placed on the path of the second beam; and means for applying to said device a pumping beam whose frequency is that of the first light beam ($\omega$) increased by the frequency of the acoustic wave (f1).

11. Imaging system in accordance with claim 10, wherein the filtering device (AMP) acts in reflection and that the system comprises a beam splitter (S') placed between the filtering device (AMP) and the medium (H) in order to return the filtered image of the medium (H) to the detector (D).

12. Imaging system in accordance with claim 4, comprising a polarizer (P) which is placed on the path of the source light beam (FS) and linearly polarizes said beam.

13. Imaging system in accordance with claim 4, wherein the detector (D) is a photodiode.

14. Imaging system in accordance with claim 4, wherein the detector (D) comprises a series of aligned detectors.

15. Imaging system in accordance with claim 4, wherein the detector (D) comprises a matrix of detectors.

16. Imaging system in accordance with claim 4, wherein it comprises a device for displaying an image of a zone of the medium (H) supplied by the first acoustic transducer (TA1), the detector (D) being also intended to permit display of an optical image of the same zone.

17. Imaging system in accordance with claim 4, comprising:

on the path of the first light beam (F1) a semi-reflecting optical device (S2) which permits transmission of the first light beam to the medium and reflects the light which comes from the medium;

another optical collimation device O' in which the object focus reflected by the semi-reflecting optical device (S2) is located at said object focus and receives the light reflected by the semi-reflecting optical collimation device;

a second detector (D2) placed on the path of the light retransmitted by the semi-reflecting optical device (S2) and the optical device (O').

18. Imaging system in accordance with claim 4, comprising:

means for shifting the optical devices which transmit the first, second and reference light beams with respect to the medium.

19. Imaging system in accordance with claim 18, wherein the shifting means comprises waveguides for transmitting the first and reference light beams.

20. Imaging system in accordance with claim 19, wherein the waveguides are optical fibers.

21. Imaging system in accordance with claim 18, comprising, on the path of the first beam (F1), a light beam translating device (TR1) which makes it possible to shift the direction of transmission of the first beam parallel to a predetermined direction.

22. Imaging system in accordance with claim 21, comprising, on the path between said beam splitter means and said detector, a second beam translating device (TR2) for shifting the direction of transmission of said reference beam parallel to a predetermined direction.

23. Imaging system in accordance with claim 22, wherein each of said first and second beam translating devices (TR1, TR2) comprises two reflection devices having reflecting surfaces which are parallel to each other and movable in rotation.

24. Imaging system in accordance with claim 22, wherein each beam translating device (TR1, TR2) comprises two reflection devices having reflecting surfaces which are parallel to each other and movable in translation.

* * * * *